United States Patent [19]

Kanai

[11] Patent Number: 5,359,906
[45] Date of Patent: Nov. 1, 1994

[54] METHOD OF PARTITIONING PARTICLE SIZE DISTRUBUTION DATUM

[75] Inventor: Kazuyuki Kanai, Kasai, Japan

[73] Assignee: Toa Medical Electronics Company, Limited, Kobe, Japan

[21] Appl. No.: 823,975

[22] Filed: Jan. 23, 1992

[30] Foreign Application Priority Data

May 9, 1991 [JP] Japan .................. 3-135979

[51] Int. Cl.$^5$ .............................. G01N 15/02
[52] U.S. Cl. .................... 73/865.5; 364/555
[58] Field of Search ............ 73/865.5; 364/555

[56] References Cited

U.S. PATENT DOCUMENTS

| | | | |
|---|---|---|---|
| 3,449,567 | 6/1969 | Olivier et al. | 73/865.5 X |
| 3,515,884 | 6/1979 | Imadate | 377/12 |
| 3,944,797 | 3/1976 | Coulter et al. | 364/555 |
| 4,128,884 | 12/1978 | England | 364/555 X |
| 4,817,446 | 4/1989 | Kanamri | 73/865.5 |

Primary Examiner—Tom Noland
Attorney, Agent, or Firm—Wegner, Cantor, Mueller & Player

[57] ABSTRACT

A method of using a technique of fuzzy inference for partioning a particle size distribution diagram indicative of a relationship between particle size and its frequency of a mixture of several kinds of granular substances, such as white blood corpuscles including lymph corpuscles, monocytes and granulocytes, to define particle size regions for the respective substances. More particularly, some estimation points are selected on the abscissa of the particle size distribution diagram and some characteristic parameters are calculated at each estimation point with the corresponding frequency. A fuzzy production rule for each characteristic parameter is applied to seek an estimated value of the estimation point and the estimated values for all characteristic parameters at each estimation point are combined to obtain a composite estimated value. The estimation point corresponding to the greatest one of all resultant composite estimated values is appointed to an objective partition point.

6 Claims, 4 Drawing Sheets

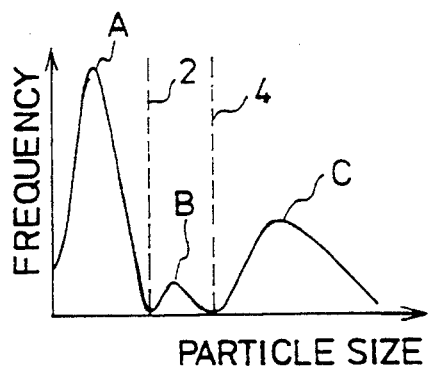
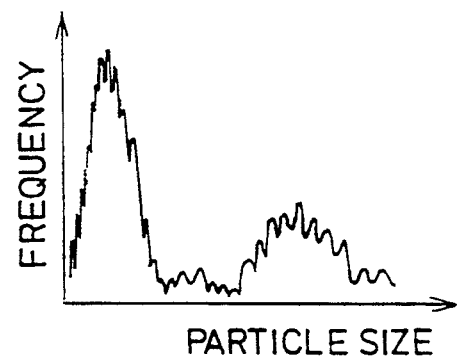
FIG. 1      FIG. 2
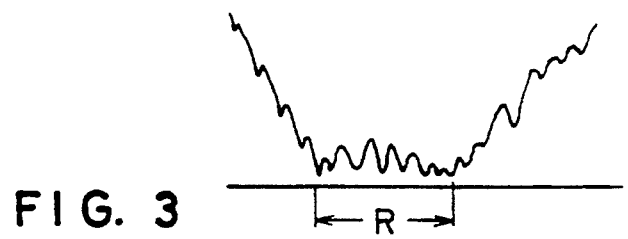
FIG. 3
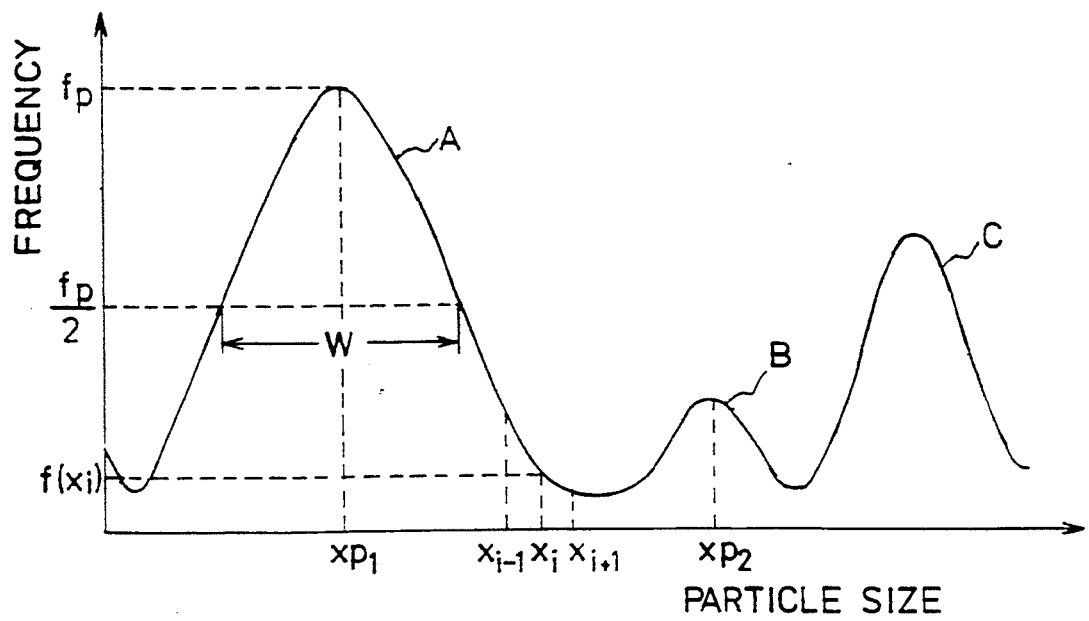
FIG. 6

METHOD OF PARTITIONING PARTICLE SIZE DISTRUBUTION DATUM

BACKGROUND OF INVENTION

This invention relates to a method of partitioning a particle size distribution diagram of a mixture of several kinds of granular substances having different mean particle sizes, that is, a method of drawing boundary lines between the distributions of respective substances and, especially, to such method using a technique of fuzzy inference in its process.

For example, white blood corpuscles are composed of a mixture of lymph corpuscles, monocytes and granulocytes and its particle size distribution diagram prepared by measuring its particle size and corresponding frequency shows a curve, as shown in FIG. 1, having three peaks A, B and C which correspond respectively to the lymph corpuscle, monocytes and granulocytes. When the number of particles of each substance is counted from this diagram it is necessary to draw partition lines 2 and 4 between the respective peaks to define the regions of respective substances. While these partition lines may be drawn from the bottoms of valleys of the distribution curve as shown, it cannot be done so simply in practice. Because the particle size distribution curve available from a conventional device such as disclosed in U.S. Pat. No. 3,515,884 has undulations as shown in FIG. 2 due to quantizing errors at the time of A/D conversion of measured particle sizes. Such a particle size distribution diagram having undulations often provides a result falling short of an expectaton of experts, when it is input in a computer to seek a position of the minimum frequency. Accordingly, it has been a general practice to execute a smoothing process, such as calculation of a moving average of the data, before patitioning or analyzing the particle size distribution as disclosed in U.S. Pat. No. 4 817 446 for example.

However, it has been impossible to completely remove the undulations by such a smoothing process and, due to such a simple definition of the partitioning position as the minimum frequency position, the above-mentioned problem has been maintained and reproducibility of the result has been very low. For example, if some undulations as shown in FIG. 3 are left in the valley of the distribution curve, the partitioning position of the computer is liable to move within a range R. Although the apparent undulations can be removed completely by enforcing the smoothing process, it is not recommended since the distribution may lose its characteristic feature.

Accordingly, an object of this invention is to provide a novel and improved method which can determine the partitioning position constantly at high reproducibility, using a particle size distribution curve having undulations as described above.

SUMMARY OF INVENTION

The above object can be attained by applying a fuzzy inference to the partitioning process in accordance with this invention.

According to the method of this invention, as schematically shown in a flow chart of FIG. 4, a one-dimensional particle size distribution diagram indicative of a relationship between the particle size and its frequency is sought first (S1) and plural points (hereinunder referred to as "estimation points") are set on its abscissa (particle size axis) to infer acceptability (hereinunder referred to as "estimated value") of each point as the partitioning position. To this end, the values of predetermined characteristic parameters are then calculated at each estimation point (S2) and a corresponding estimated value is sought in accordance with a production rule indicative of the relationship between each characteristic parameter and the estimated value (S3). Then all the estimated values at each estimation point are combined to obtain a composite estimated value (S4) and the estimation point corresponding to the maximum one of all composite estimated values is appointed to the partioning position (S5).

According to a feature of this invention, the above-mentioned characteristic parameters include, at least, a below-mentioned relative frequency at the estimation point (hereinunder referred to as "first characteristic parameter"), a sum of frequencies within a small particle size interval around the estimation point inclusive (hereinunder referred to as "second characteristic parameter") and an below-mentioned quantity relating to a distance between the estimation point in problem and the estimation point corresponding to the maximum frequency (hereinunder referred to as "third characteristic parameter"). According to the above-mentioned production rules the estimated value is high if the first characteristic parameter is small, the estimated value is high if the second characteristic parameter is small and the estimated value is high if the third characteristic parameter is close to a predetermined value.

According to another feature of this invention, the above characteristic parameters may further include an absolute frequency at the estimation point (hereinunder referred to as "fourth characteristic parameter"), a gradient of the distribution curve at the estimation point (herein-under referred to as "fifth characteristic parameter") and/or a difference of sum frequencies within two small particle size intervals in both sides of the estimation point (hereinunder referred to as "sixth characteristic parameter"). According to the production rules in these cases, the estimated value is high if the fourth characteristic parameter is small, the estimated value is high if the fifth characteristic parameter is small and the estimated value is high if the sixth characteristic parameter is small.

According to a further feature of this invention the converses of the above production rules can be used also.

These features of this invention will be described in more detail below about an embodiment thereof with reference to the accompanying drawings.

BRIEF DESCRIPTION OF DRAWINGS

In the drawings:

FIG. 1 is a diagram showing a schema of particle size distribution of white blood corpuscles;

FIG. 2 is a diagram showing a particle size distribution curve having undulations obtained by a conventional measuring device;

FIG. 3 is an enlarged view of a part of a valley of the particle size distribution curve of FIG. 2 to which a smoothing process is applied;

FIG. 6 is a diagram showing an example of the particle size distribution curve partitioned in the above embodiment;

DESCRIPTION OF PREFERRED EMBODIMENT

Figure 4:
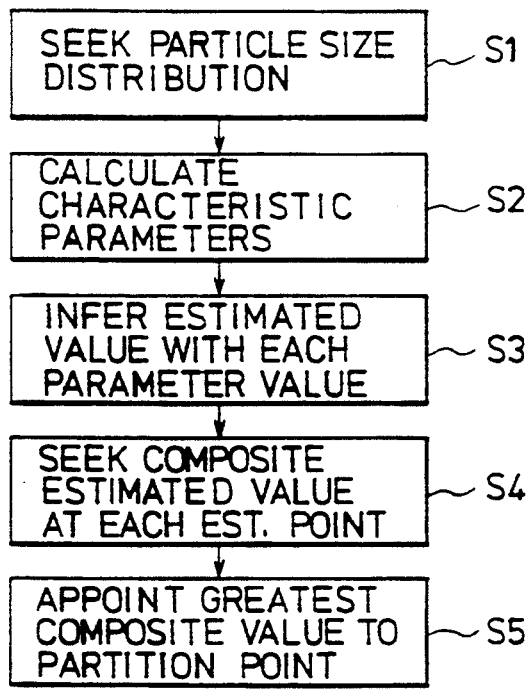
FIG. 4 is a flow chart showing a schema of the partitioning process according to the method of this invention.
Figure 5:
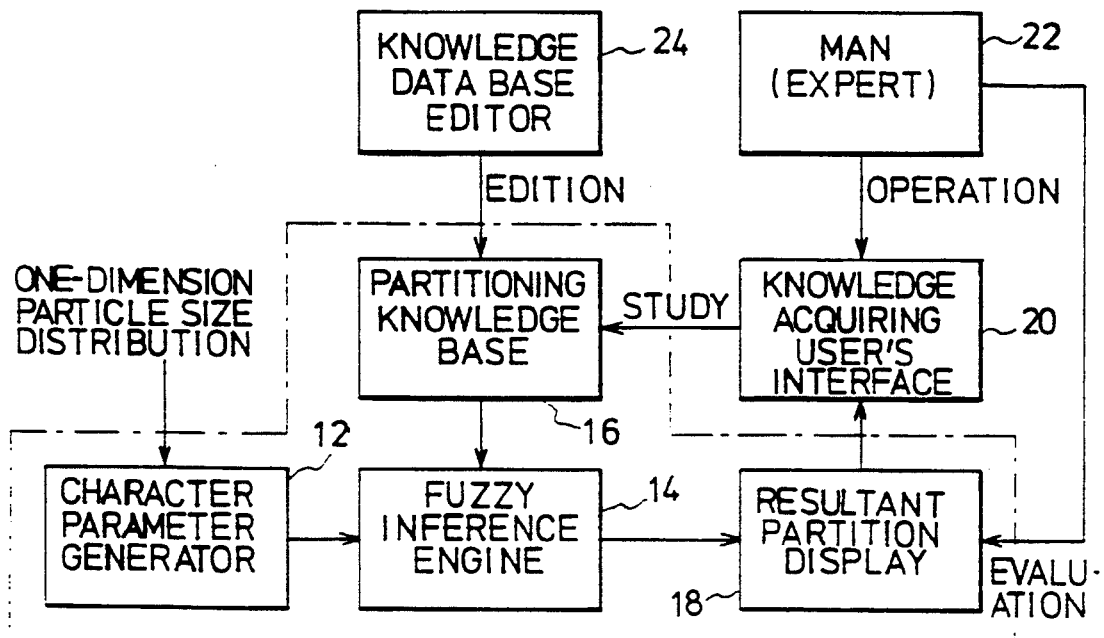
FIG. 5 is a block diagram showing a device used in an embodiment of the method of this invention.

In FIG. 5 a phantom block 10 containing functional elements 12, 14 16 and 18 is a basic section for applying fuzzy inference to a particle size distribution datum to determine its partition points in accordance with the method of this invention. More particularly, a characteristic parameter generator 12 receives a one-dimensional particle size distribution datum as shown in FIG. 6, for example from a particle size counting device (not shown) as described above, and derives therefrom various characteristic parameters as described below. These characteristic parameters are supplied to a fuzzy inference engine 14. The fuzzy inference engine 14 is also supplied from a partioning knowledge base 16 with below-mentioned membership functions. The fuzzy inference engine 14 applies fuzzy inference to the characteristic parameters based upon the membership functions to determine the partition points as described below. The resultant partition points are then displayed by a resultant partition display 18. The resultant partition display 18 can also display, at the same time, a folded line diagram which shows an estimated value indicative of the likelihood of each partition point.

The functional elements outside the phantom block 10 of FIG. 5 serve additional functions for the above basic section 10. More particularly, a knowledge acquiring user's interface 20 serves to compare the partition point determined by the basic section 10 and displayed by the display 18 with a partition point selected by an expert in this field and to correct the membership functions and like so as to reduce the difference therebetween. A knowledge base editor 24 serves to initialize the partitioning knowledge base 16 for such knowledge bases as membership functions and production rules and also to effect correction, supplementation and cancellation thereof.

The characteristic parameter generator 12 derives six characteristic parameters for example from the one-dimensional particle size distribution datum of FIG. 6. The particle size distribution diagram is drafted by selecting N values of particle size as estimation points $x_i(i=1,2,...N)$ and counting the frequency of particle size at each estimation point. In this embodiment, the number N is set to 256. Although the actual curve has many undulations as shown in FIG. 2 such undulations are not shown in FIG. 6 for convenience of explanation. While the characteristic parameters may be derived at all estimation points, it is not always needed. In other words, when a partition point is to be determined between the peaks A and B of FIG. 6, for example, it is enough to derive them at the estimation points $x_i$ between an estimation point $x_{p1}$ corresponding to the top of the peak A and an estimation point $x_{p2}$ corresponding to the top of the peak B.

The characteristic parameter generator 12 derives first the frequency $f(x_i)$ or absolute frequency at each estimation point $x_i$ as one of the characteristic parameters. The reason for selecting the absolute frequency $f(x_i)$ as a characteristic parameter is that its value generally becomes minimum at a point which is likely in the bottom of a valley. However, when the maximum frequencies of the peaks A and B are extremely large and the other frequencies are relatively small and not so different from each other, that is, when the valley is relatively flat and broad, the absolute frequency is lacking in reliability as a characteristic parameter. Therefore, the characteristic parameter generator 12 derives a relative frequency of an alternative characteristic parameter. Here, the relative frequency means a percentage of the frequency at each estimation point with respect to the greatest absolute frequency, that is the frequency $f_r(x_i)$ given by the following equation.

$$f_r(x_i) = f(x_i) \times 100/f_p \tag{1}$$

While this value relates to the magnitude of absolute frequency $f(x_i)$ with respect to the absolute frequency $f_p$, it assumes a same value regardless of the values of $f(x_i)$ and $f_p$ if the ratio thereof is fixed. Therefore it is undesirable to use it alone as a condition of estimation and it is recommendable to use it with the absolute frequency.

The characteristic parameter generator 12 further derives a sum of frequencies at $2n+1$ estimation points around the estimation point $x_i$ inclusive as a characteristic parameter. This value $f_s(x_i)$ is given by the following equation.

$$f_s(x_i) = \sum_{j=i-n}^{i+n} f(x_j) \tag{2}$$

where n is an integer selected experientially. It can be said on this characteristic parameter that the smaller the value thereof, the nearer the bottom of the valley the estimation point $x_i$ is, even if the particle size distribution has undulations.

The characteristic parameter generator 12 also derives a mean gradient of the particle size distribution curve within a small interval including the estimation point $x_i$ as a charactertistic parameter. This value $f_g(x_i)$ is given by the following equation.

$$f_g(x_i) = \frac{f(x_{i+m}) - f(x_{i-m})}{2m} \tag{3}$$

where m is an integer selected experientially. This value can be used as a characteristic parameter since the smaller it is, the more likely it is the bottom of the valley.

The characteristic parameter generator 12 may derive also a certain value relating to the distance between the estimated point $x_i$ and the above-mentioned peak point $x_{pl}$ as a characteristic parameter This value $f_w(x_i)$ is given by the following equation, for example.

$$f_w(x_i) = \frac{|x_i - x_{p1}|}{W} \quad (4)$$

where W is a width of the peak of particle size distribution at its half height $f_p/2$ as shown in FIG. 6. It has been known experientially that the nearer this value draws to a specific value, the nearer the estimation point $x_i$ draws to the bottom of valley.

The characteristic parameter generator 12 may further derive a difference between two sums of frequencies within two small intervals on both sides of the estimation point $x_i$ as a characteristic parameter. This value $f_d(x_i)$ is given by the following equation.

$$f_d(x_i) = \left| \sum_{j=i-k}^{i} f(x_j) - \sum_{j=i}^{i+k} f(x_j) \right| \quad (5)$$

where k is an integer selected experientiatly. This characteristic parameter is effective to locate the partition point in the middle of two peaks in such a case where the valley therebetween is relatively flat and linear.

Fuzzy production rules indicative of the relationships of these characteristic parameters and the aforementioned estimated value and antecedent and conclusive membership functions of the respective production rules are determined by those skilled in this field and previously fed from the knowledge data base editor 24 into the partitioning knowledge base 16 and stored therein. The fuzzy inference engine 14 reads these membership functions in accordance with the characteristic parameter values supplied from the characteristic parameter generator 12 and executes a fuzzy inference operation as described below.

Figure 7A:
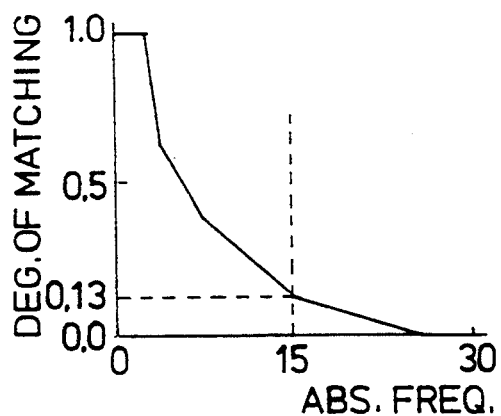
FIGS. 7a and 7b are diagrams respectively showing antecedent and conclusive membership functions of a fuzzy production rule used in the above embodiment.
Figure 7B:
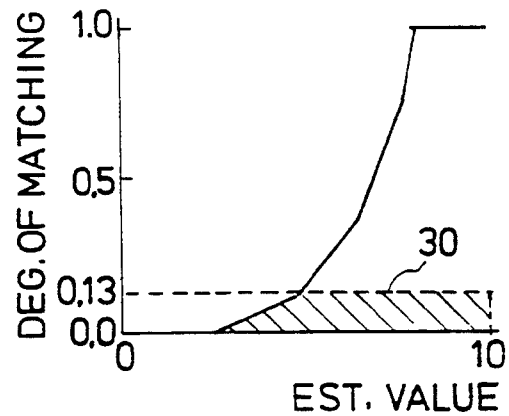
Figure 9A:
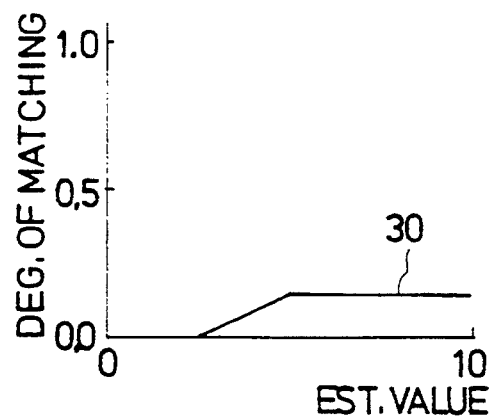
FIGS. 9a and 9b are diagrams respectively showing the conclusive membership functions of FIGS. 7b and 8b corrected in accordance with the value of a characteristic parameter.

For example, in the case of using the aforementioned absolute frequency as a characteristic parameter, such a proposition as "If the absolute frequency is small, the estimated value is high." is obtained as a production rule. In this case, the antecedent membership function reading "the absolute frequency is small" is given experientially as shown in FIG. 7a and the conclusive membership function reading "the estimated value is high" is given experientially as shown in FIG. 7b. Supposing now the absolute frequency from the characteristic parameter generator 12 is 15 for example, it is found from the antecedent membership function of FIG. 7a that its degree of matching is 0.13. Then, the "head" of the conclusive membership function of FIG. 7b is cut off at the level of 0.13 of the degree of matching to obtain a corrected pattern 3C FIG. 9n. Such conclusion discounting method by "head-cutting" is well known in the art and will not be described in further detail.

Figure 8A:
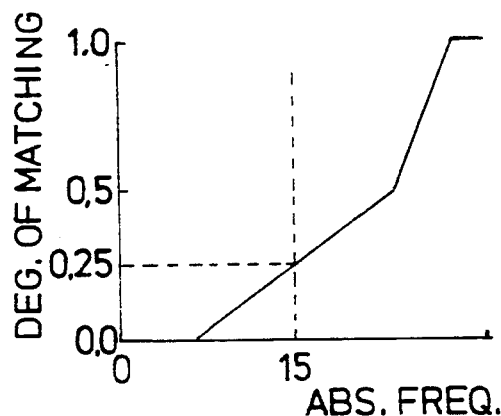
FIGS. 8a and 8b are diagrams respectively showing antecedent and conclusive membership functions of a converse of the above production rule also used in the same embodiment.
Figure 8B:
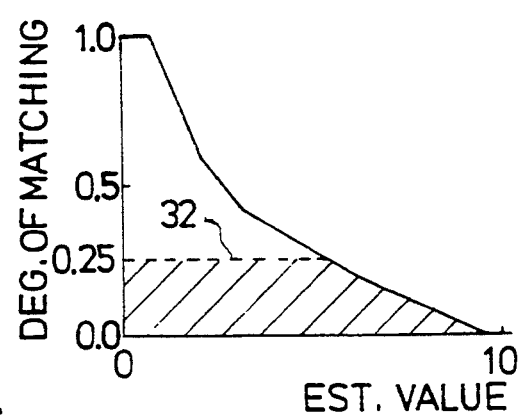
Figure 9B:
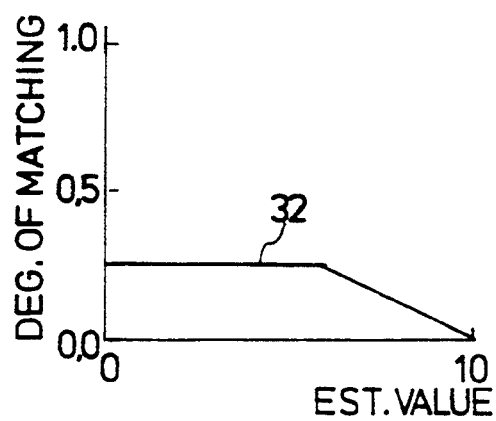

Next, for considering about inconsistent production rules at the same time, similar inference is made in accordance with a production rule reading "If the absolute frequency is large, the estimated value is low" which is the converse proposition of the above-mentioned production rule. In this case, an antecedent membership function reading "the absolute value is large" of FIG. 8a and a conclusive membership function reading "the estimated value is low" of FIG. 8b are used. As the degree of matching corresponding to the absolute frequency of 15 is now 0.25 as shown in FIG. 8a the "head-cutting" of the conclusive membership function is effected at this level as shown in FIG. 8b and a corrected pattern 32 of FIG. 9b is obtained.

Figure 9C:
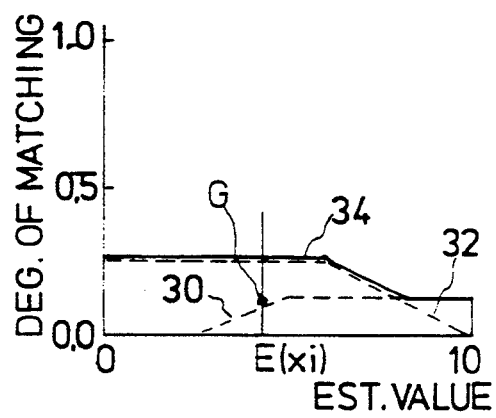
FIG. 9c is a diagram illustrative of a procedure of combining the diagram of FIGS. 9a and 9b to obtain a composite estimated value.

Both corrected conclusive membership functions 30 and 32 obtained as above are then combined into a logical sum to result in a pattern 34 as shown in FIG. 9c, which represents the composite estimated value. While there are several methods for defuzziying this pattern into a single composite estimated value, the center of gravity G of the pattern 34 is sought in this embodiment and the abscissa $E(x_i)$ of the center of gravity is appointed to the composite estimated value of the estimation point $x_i$. Such defuzzification using this center of gravity method is also well known in the field of fuzzy inference and, therefore, no further detailed description will be made here. Such composite estimated value is sought in the same fashion at each estimation point and the estimation point corresponding to the greatest one of them is appointed to the objective partition point.

While, in the above embodiment the logic sum of the two resultant corrected membership functions has been sought with the production rule relating to a specific characteristic parameter, namely, the absolute frequency and with its converse proposition, some of the other characteristic parameters as above mentioned may be used at the same time. The production rules for these characteristic parameters are determined as follows, for example. "If the relative frequency $f_r(x_i)$ is small the estimated value is high.", "If the relative frequency $f_r(x_i)$ is large, the estimated value is low.", "If the sum of frequencies within the adjoining small interval $f_s(x_i)$ is small the estimated value is high.", "If the sum of frequencies within within the adjoining small interval $f_s(x_i)$ is large, the estimated value is low.", "If the gradient of the adjoining small interval $f_g(x_i)$ is small the estimated value is high.", "If the gradient of the adjoining small interval $f_g(x_i)$ is large, the estimated value is low.", "If the departure from the peak $f_w(x_i)$ is close to a predetermined value, the estimated value is high.", "If the departure from the peak $f_w(x_i)$ is not close to a predetermined value, the estimated value is low.", "If the difference between two sums of frequencies within two small intervals on both sides $f_d(x_i)$ is small, the estimated value is high." and "If the difference between two sums of frequencies within two small intervals on both sides $f_d(x_i)$ is large, the estimated value is low.". When two or more characteristic parameters are used, the conclusive membership functions based upon the respective production rules are "head cut" with the orders of matching of the respective characteristic parameters according to the respective antecedent membership functions to obtain four or more corrected patterns and a logic sum of the resultant patterns is sought to prepare a composite estimated pattern It is not always necessary to use all of the above-mentioned six characteristic parameters and it is enough to use three of them that is $f_r(x_i)$, $f_s(x)$ and $f_w(x_i)$.

While a logic sum of the corrected conclusive membership functions is used in the above embodiment an algebraic sum may be used also. While the conclusive membership function is corrected by "head cutting" in accordance with the degree of matching of the characteristic parameter value, any correcting method well known in the fuzzy inference technique may be used also. While the center-of-gravity method is used for defuzzification of the composite estimated value, any known method such as median method may be used also.

In contrast to the prior art method using crisp inference which appoints for example a minimum frequency point to the partition point, the particle size distribution partitioning method of this invention using fuzzy inference can provide a result which is less affected by the undulations of the distribution curve and very close to an expert's conclusion, since the inference is executed in consideration of plural characteristic parameters.

I claim:

1. A method for determining partition points in order to establish boundaries between ranges of various substances of a mixture of plural kinds of granular substances, and comprising the steps of:

measuring sizes and corresponding frequencies of occurrence of particles of said substances;

obtaining a particle size distribution based upon said measuring and indicative of a relationship between size and frequency of said particles of said mixture;

selecting a plurality of particle size values of said particle size distribution;

calculating values of a plurality of predetermined characteristic parameters for each of said particle size values, seeking an estimated value of each of said particle size values as each partition point for the respective characteristic parameter values based upon fuzzy production rules respectively prescribing relationships between said characteristics parameter values and said estimated values, combining said estimated values for said characteristic parameters of each particle size value to seek a composite estimated value for said particle size value, and appointing a particle size value corresponding to a greatest one of said composite estimated values for all of said selected particle size values to said partition point, said characteristic parameters including a first characteristic parameter which is a relative frequency of a frequency of each said particle size value with respect to a greatest frequency, a second characteristic parameter which is a sum of a frequencies corresponding to a particle size values within a small interval including each said particle size, and a third characteristic parameter which is a value relating to a difference between each said particle size value and a particle size value corresponding to said greatest frequency, said fuzzy production rules comprising prescribing respectively that the estimated value is high if the first characteristic parameter value is small, that the estimated value is high if the second characteristic parameter value is small, and that the estimated value is high if the third characteristic parameter value is close to a predetermined value.

2. A method as set forth in claim 1, characterized in that said fuzzy production rules further comprise prescribing respectively that the estimated value is low if the first characteristic parameter value is large, that the estimated value is low if the second characteristic parameter value is large, and that the estimated value is low if the third characteristic parameter value is not close to a predetermined value.

3. A method as set forth in claim 2, characterized in that said characteristic parameters further comprise at least one characteristic parameter selected from a group consisting of a fourth characteristic parameter which is the frequency corresponding to said each particle size value, a fifth characteristic parameter which is a gradient of the particle size distribution within a small interval including said each particle size value, and a sixth characteristic parameter which is a difference between sums of the frequencies within two small intervals in both sides of each said particle size value, and said fuzzy production rules comprise at least one production rule selected from rules prescribing respectively that the estimated value is high if the fourth characteristic parameter value is small, that the estimated value is high if the fifth characteristic parameter value is small, and that the estimated value is high if the sixth characteristic parameter value is small.

4. A method as set forth in claim 2, characterized in that said characteristic parameters further comprise at least one characteristic parameter selected from a group consisting of a fourth characteristic parameter which is the frequency corresponding to said each particle size value, a fifth characteristic parameter which is a gradient of the particle size distribution within a small interval including said each particle size value, and a sixth characteristic parameter which is a difference between sums of the frequencies within two small intervals in both sides of each said particle size value, and said fuzzy production rules further comprise at least one production rule selected from rules prescribing respectively that the estimated value is high if the fourth characteristic parameter value is small, that the estimated value is high if the fifth characteristic parameter value is small, and that the estimated value is high if the sixth characteristic parameter value is small, and at least one of a set of rules prescribing respectively that the estimated value is low if the fourth characteristic parameter value is large, that the estimated value is low if the fifth characteristic parameter value is large, and that the estimated value is low if the sixth characteristic parameter value is large.

5. A method as set forth in claim 1, characterized in that said characteristic parameters further comprise at least one characteristic parameter selected from a group consisting of a fourth characteristic parameter which is the frequency corresponding to said each particle size value, a fifth characteristic parameter which is a gradient of the particle size distribution within a small interval including said each particle size value, and sixth characteristic parameter which is a difference between sums of frequencies within two small intervals on both sides of each said particle size value, and said fuzzy production rules comprise at least one production rule selected from rules prescribing respectively that the estimated value is high if the fourth characteristic parameter value is small, that the estimated value is high if the fifth characteristic parameter value is small, and that the estimated value is high if the sixth characteristic parameter value is small.

6. A method as set forth in claim 5, characterized in that said fuzzy production rules further comprise at least one of a set of rules prescribing respectively that the estimated value is low if the fourth characteristic parameter value is large, that the estimated value is low if the fifth characteristic parameter value is large, and that the estimated value is low if the sixth characteristic parameter value is large.

* * * * *